(12) United States Patent
Keyer et al.

(10) Patent No.: US 7,491,207 B2
(45) Date of Patent: Feb. 17, 2009

(54) ROD PERSUADER

(75) Inventors: Thomas R. Keyer, Aston, PA (US); Larry Binder, Langhorne, PA (US); Martin Walther, Thomery (FR)

(73) Assignee: Synthes USA, LLC, West Chester, PA (US)

( * ) Notice: Subject to any disclaimer, the term of this patent is extended or adjusted under 35 U.S.C. 154(b) by 371 days.

(21) Appl. No.: 10/822,599

(22) Filed: Apr. 12, 2004
(Under 37 CFR 1.47)

(65) Prior Publication Data
US 2005/0228392 A1    Oct. 13, 2005

(51) Int. Cl.
*A61B 17/90* (2006.01)
(52) U.S. Cl. .................................... 606/103
(58) Field of Classification Search ............... 606/61, 606/73, 86, 99, 103, 205, 207, 206, 208, 606/209; 81/421–423
See application file for complete search history.

(56) References Cited

U.S. PATENT DOCUMENTS

| | | | |
|---|---|---|---|
| 3,604,487 A | 9/1971 | Gilbert | |
| 4,050,464 A | 9/1977 | Hall | |
| 4,271,836 A | 6/1981 | Bacal et al. | |
| 4,347,845 A | 9/1982 | Mayfield | |
| 4,409,968 A | 10/1983 | Drummond | |
| 4,411,259 A | 10/1983 | Drummond | |
| 4,422,451 A | 12/1983 | Kalamchi | |
| 4,567,884 A | 2/1986 | Edwards | |
| 4,829,805 A * | 5/1989 | Koehn | 72/409.12 |
| 5,020,519 A | 6/1991 | Hayes et al. | |
| 5,060,365 A | 10/1991 | Lanzo | |
| D331,625 S | 12/1992 | Price et al. | |
| 5,167,662 A | 12/1992 | Hayes et al. | |
| 5,190,550 A | 3/1993 | Miller et al. | |
| 5,246,442 A | 9/1993 | Ashman et al. | |
| 5,281,223 A | 1/1994 | Ray | |
| 5,282,302 A | 2/1994 | Starks et al. | |
| D346,217 S | 4/1994 | Sparker et al. | |
| 5,318,589 A * | 6/1994 | Lichtman | 606/205 |
| 5,364,397 A | 11/1994 | Hayes et al. | |
| 5,385,565 A | 1/1995 | Ray | |

(Continued)

FOREIGN PATENT DOCUMENTS

DE    4238339    5/1994

(Continued)

*Primary Examiner*—Eduardo C Robert
*Assistant Examiner*—Richard Shaffer
(74) *Attorney, Agent, or Firm*—Stroock & Stroock & Lavan LLP

(57) ABSTRACT

A surgical instrument is provided for urging a longitudinal spinal member into a top-loading spinal implant. The instrument may comprise a holder assembly having a pair of fingers sized and configured to engage the underside of an edge of the spinal implant, a release assembly, and an actuating member. The release assembly may comprise a tubular member and a pusher member, the tubular member being sized and configured to be slidably disposed within the holder assembly, and the pusher member being sized and configured to slidably surround at least a portion of the holder assembly. Upon movement of the actuating member, the holder assembly and the release assembly are moveable with respect to one another so that the longitudinal spinal rod, which is engaged to the pusher member, is urged into engagement with the rod-receiving channel of the spinal implant.

19 Claims, 9 Drawing Sheets

U.S. PATENT DOCUMENTS

| | | |
|---|---|---|
| 5,430,919 A | 7/1995 | Starks et al. |
| D363,545 S | 10/1995 | Miller |
| 5,509,596 A | 4/1996 | Green et al. |
| 5,520,704 A | 5/1996 | Castro et al. |
| 5,688,274 A * | 11/1997 | Errico et al. .................. 606/61 |
| 5,707,371 A | 1/1998 | Metz-Stavenhagen |
| 5,720,751 A | 2/1998 | Jackson |
| 5,733,285 A * | 3/1998 | Errico et al. .................. 606/61 |
| 5,782,830 A | 7/1998 | Farris |
| 5,810,878 A | 9/1998 | Burel et al. |
| 5,899,901 A | 5/1999 | Middleton |
| 5,910,141 A | 6/1999 | Morrison et al. |
| 5,941,885 A | 8/1999 | Jackson |
| 6,015,409 A | 1/2000 | Jackson |
| 6,015,413 A | 1/2000 | Faccioli et al. |
| 6,017,342 A | 1/2000 | Rinner |
| 6,036,692 A | 3/2000 | Burel et al. |
| 6,123,707 A | 9/2000 | Wagner |
| 6,139,549 A | 10/2000 | Keller |
| 6,183,472 B1 | 2/2001 | Lutz |
| 6,440,133 B1 | 8/2002 | Beale et al. |
| 6,516,505 B1 | 2/2003 | Taylor |
| 6,517,554 B1 | 2/2003 | Zhu et al. |
| 6,530,929 B1 | 3/2003 | Justis et al. |
| 6,551,316 B1 * | 4/2003 | Rinner et al. .................. 606/57 |
| 6,641,595 B1 | 11/2003 | Moran et al. |
| 6,648,888 B1 | 11/2003 | Shluzas |
| 6,660,006 B2 | 12/2003 | Markworth et al. |
| 6,660,010 B2 | 12/2003 | Gellman |
| 6,712,819 B2 | 3/2004 | Zucherman |
| 6,723,100 B2 | 4/2004 | Biedermann |
| 6,726,692 B2 | 4/2004 | Bette |
| 6,743,231 B1 | 6/2004 | Gray et al. |
| 6,746,449 B2 | 6/2004 | Jones et al. |
| 2001/0027318 A1 | 10/2001 | Oribe et al. |
| 2002/0019633 A1 | 2/2002 | Ray |
| 2002/0095153 A1* | 7/2002 | Jones et al. .................. 606/61 |
| 2002/0099377 A1 | 7/2002 | Zucherman et al. |
| 2002/0139423 A1* | 10/2002 | Roethel .................. 137/614.03 |
| 2002/0161368 A1 | 10/2002 | Foley et al. |
| 2002/0169448 A1 | 11/2002 | Vanacker |
| 2003/0009168 A1 | 1/2003 | Beale et al. |
| 2003/0018342 A1 | 1/2003 | Oribe et al. |
| 2003/0023243 A1 | 1/2003 | Biedermann et al. |
| 2003/0040746 A1 | 2/2003 | Mitchell et al. |
| 2003/0060826 A1 | 3/2003 | Foley et al. |
| 2003/0225408 A1 | 12/2003 | Nichols et al. |
| 2003/0229355 A1 | 12/2003 | Keller |
| 2004/0049191 A1 | 3/2004 | Markworth et al. |

FOREIGN PATENT DOCUMENTS

| | | |
|---|---|---|
| DE | 19828137 | 1/2000 |
| FR | 2677242 | 12/1992 |
| FR | 2729291 | 7/1996 |
| WO | WO 9311715 | 6/1993 |
| WO | WO 9844858 | 10/1998 |
| WO | WO 3028566 | 4/2003 |

* cited by examiner

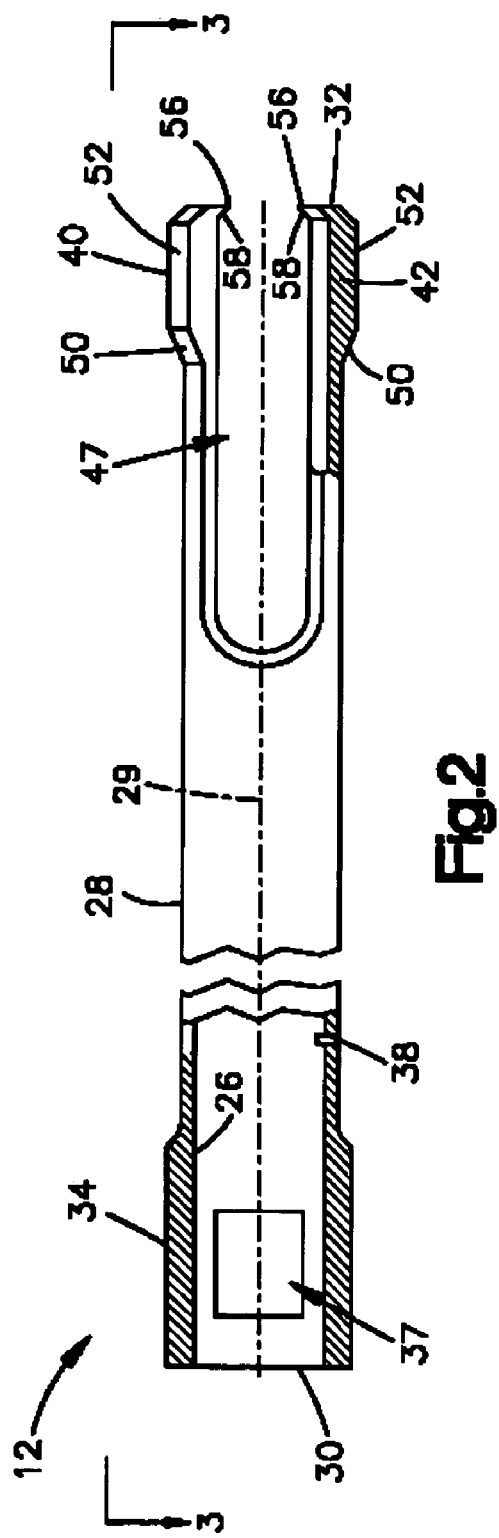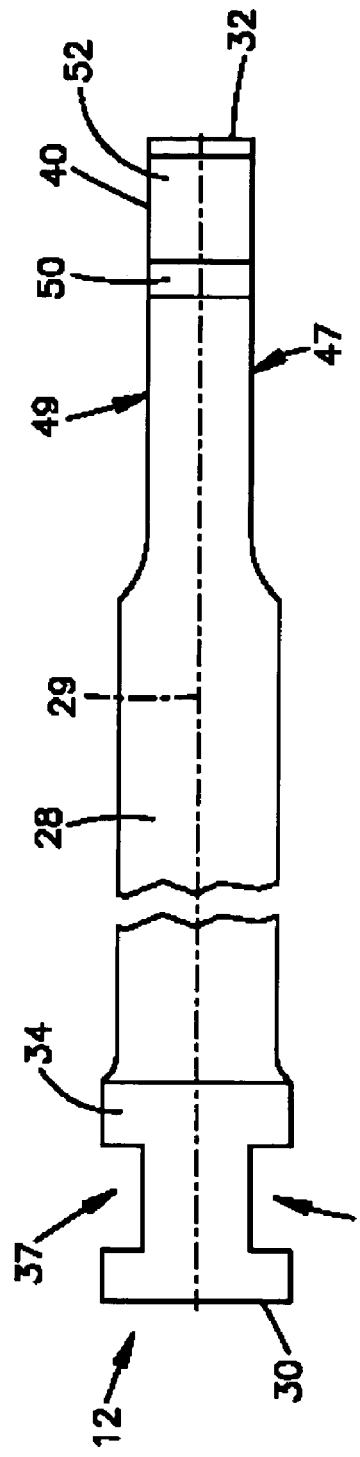

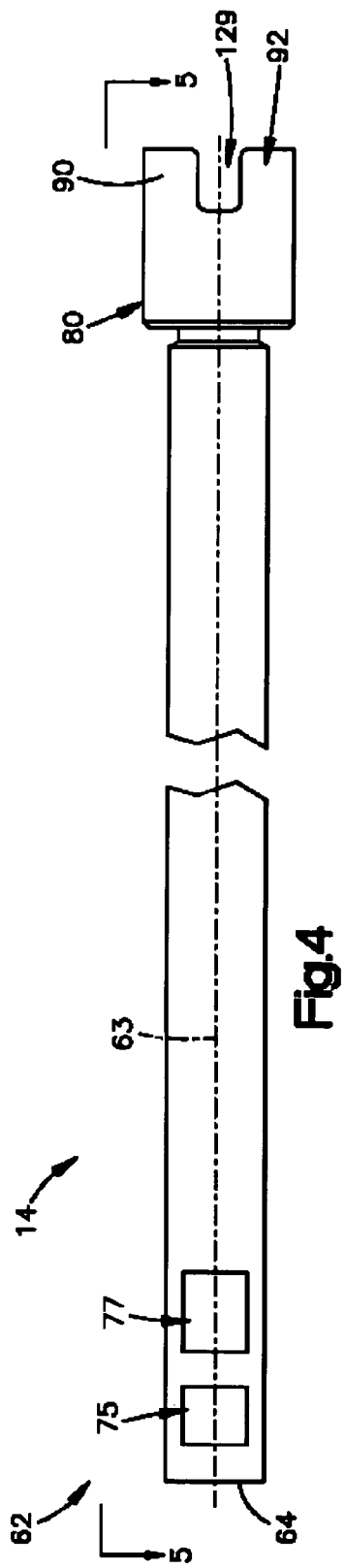
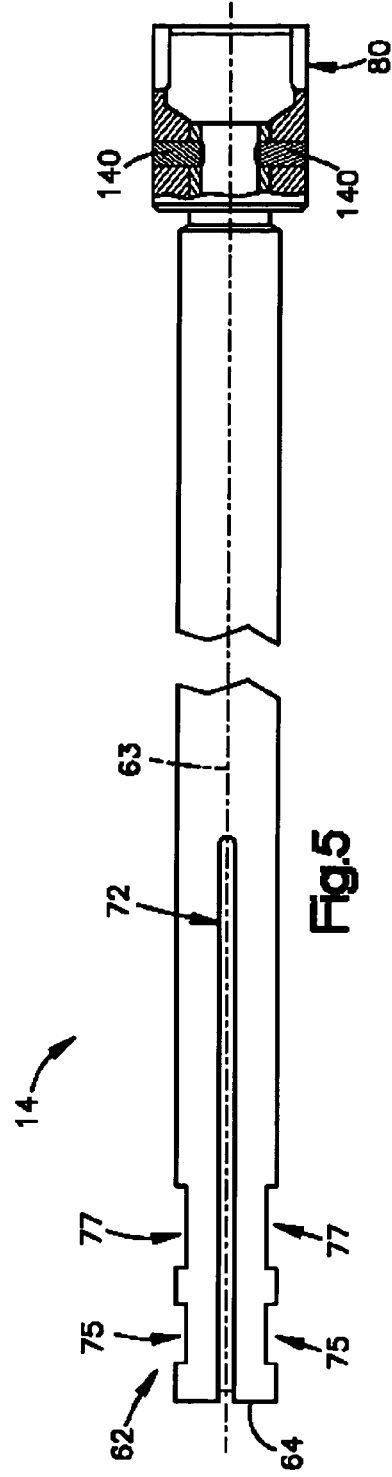

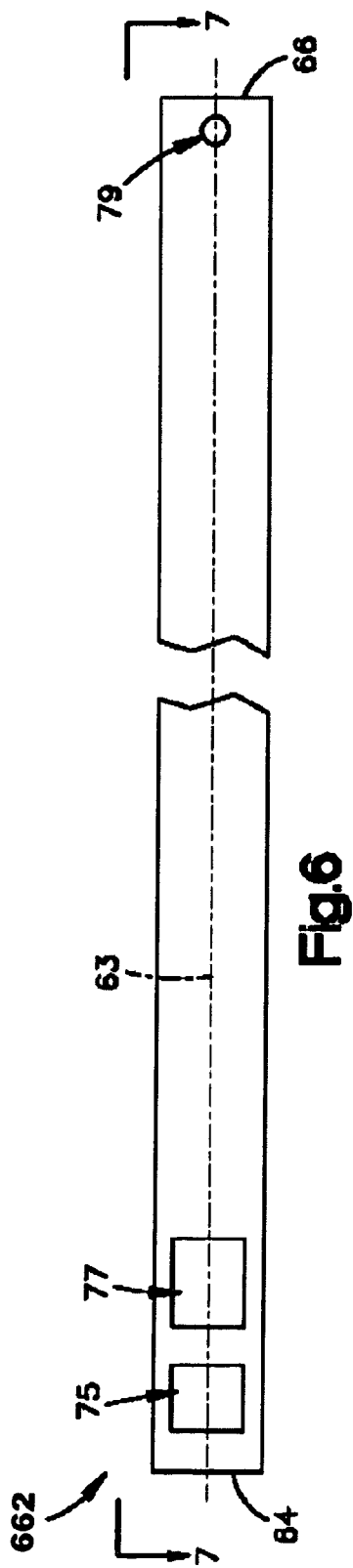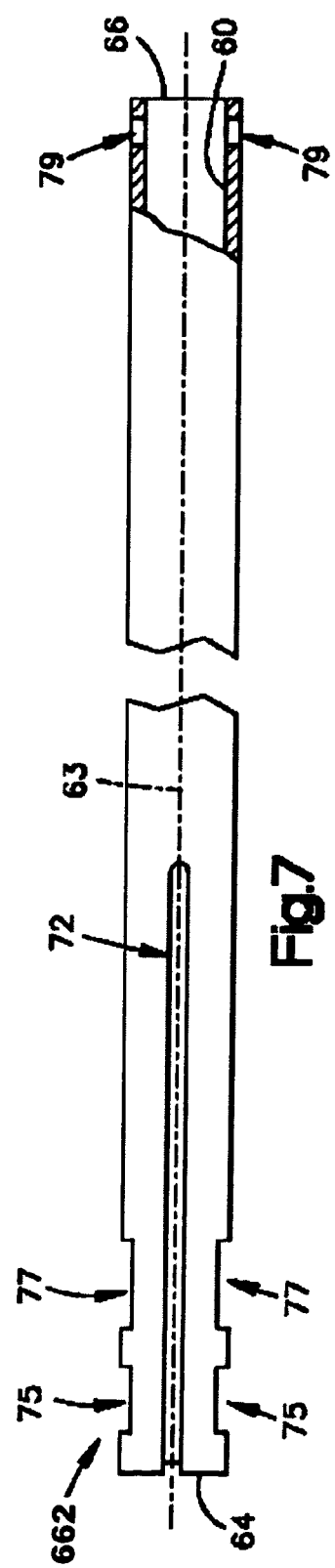

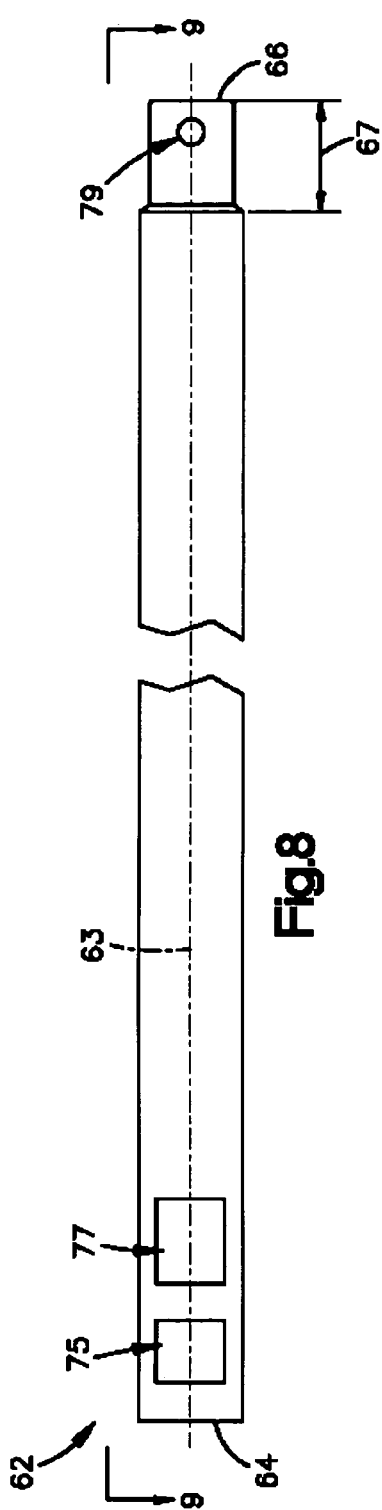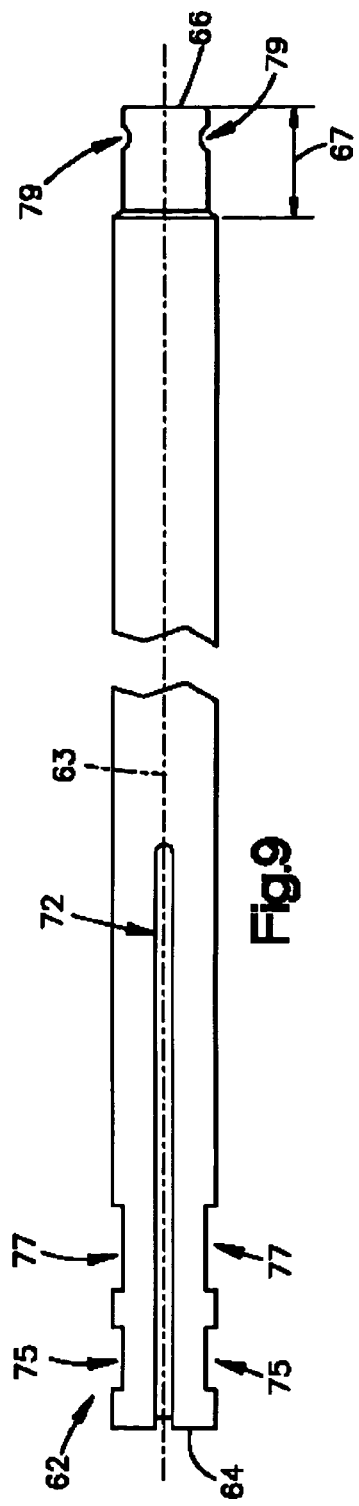

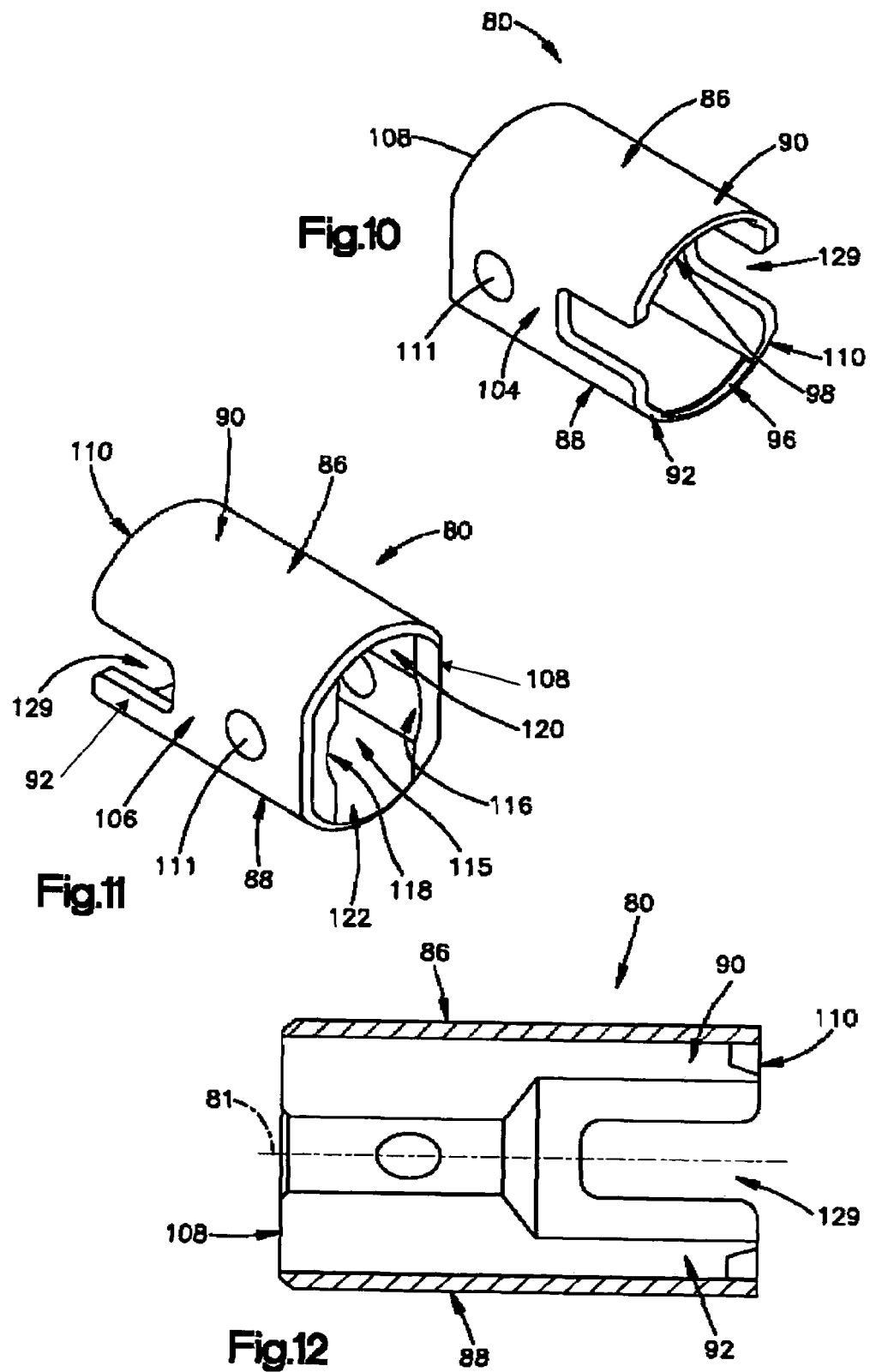

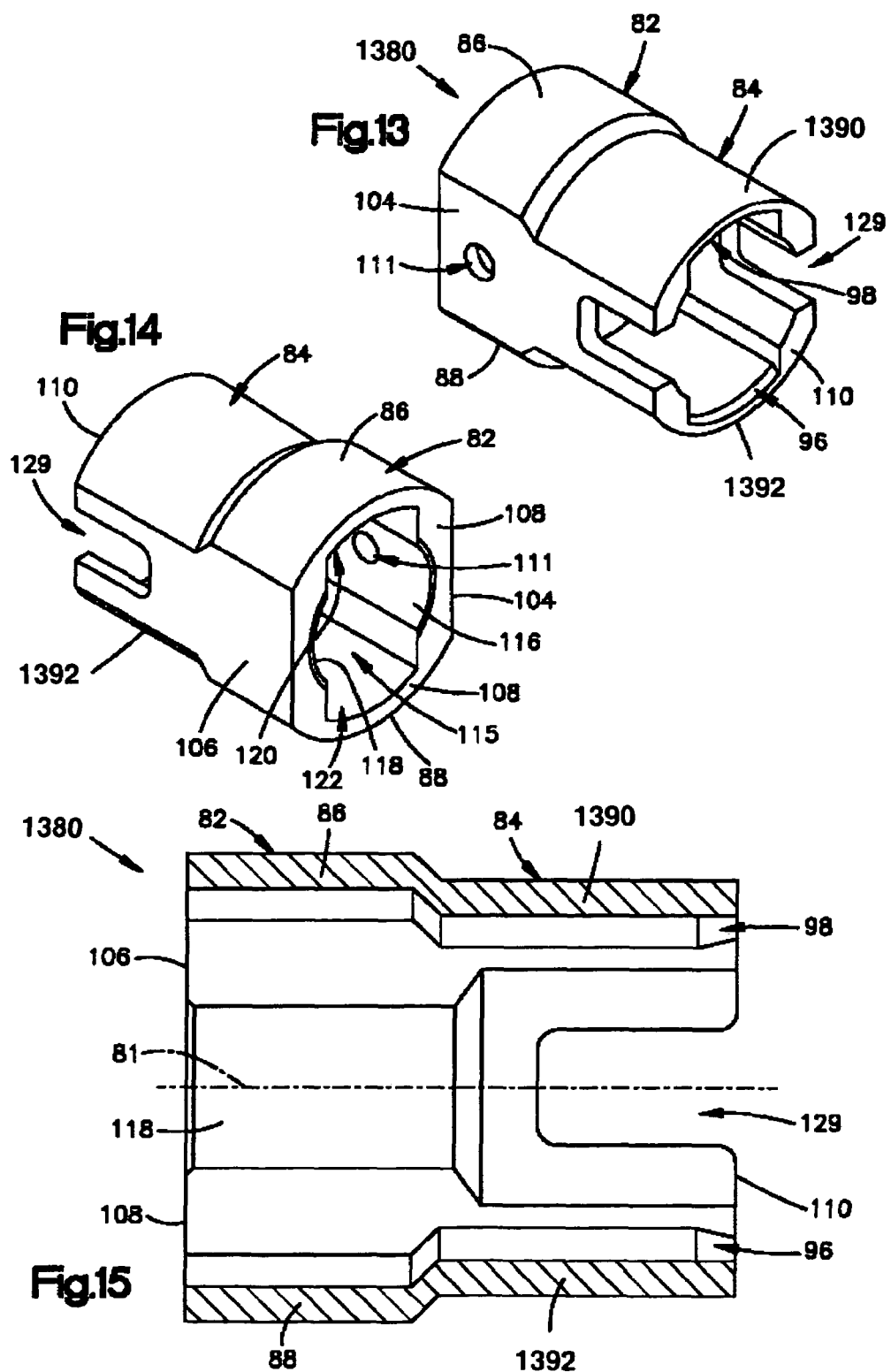

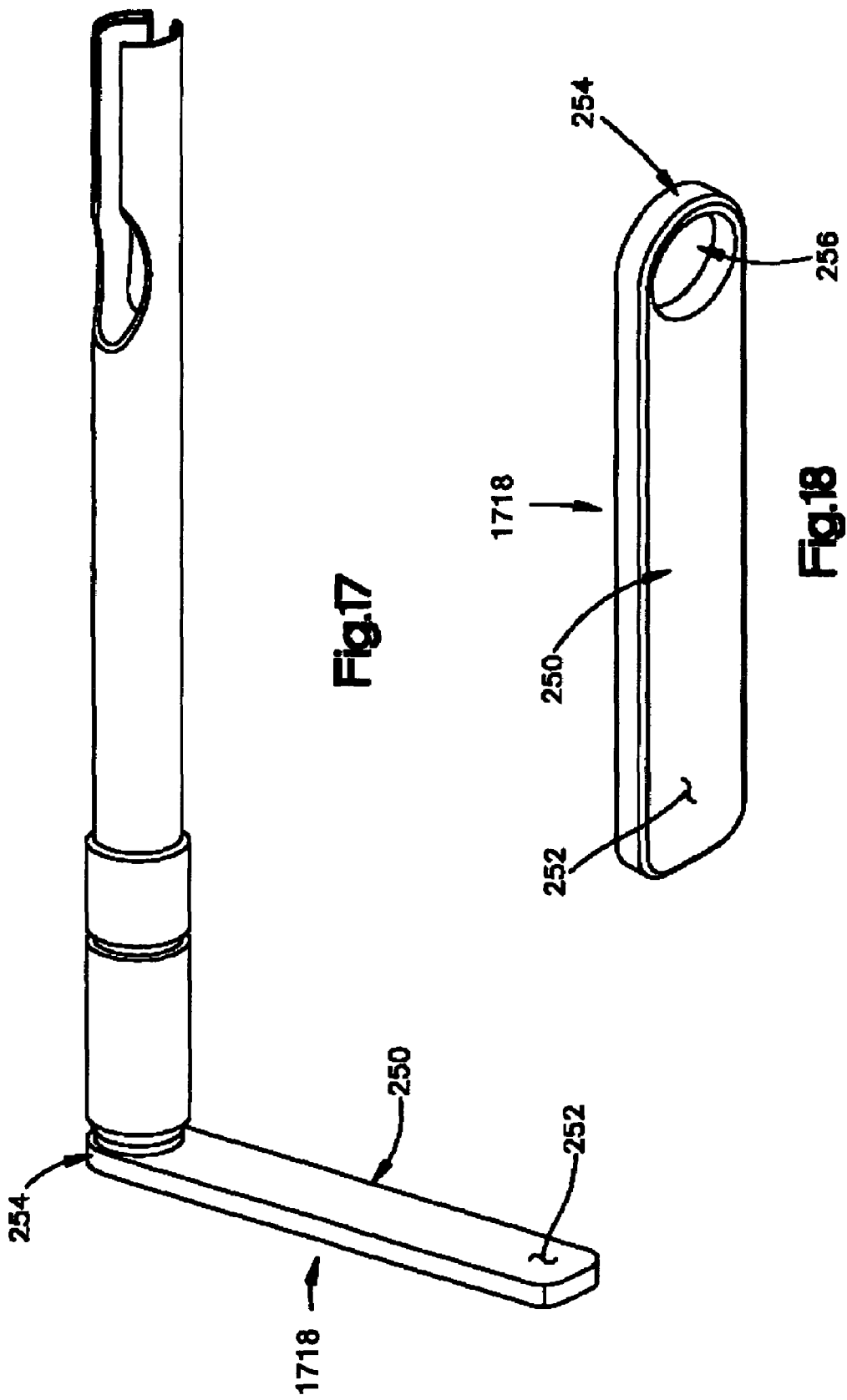

ROD PERSUADER

TECHNICAL FIELD

The present invention relates generally to surgical instruments for spinal surgery. More specifically, the present invention relates to a rod persuader for urging a longitudinal spinal rod into a rod-receiving channel of a vertebra engaging spinal implant.

BACKGROUND

It is often necessary due to various spinal disorders to surgically correct and stabilize spinal curvatures, or to facilitate spinal fusion. Numerous systems for treating spinal disorders have been disclosed. One known method involves a pair of elongated members, typically spinal rods, longitudinally placed on the posterior spine on either side of spinous processes of the vertebral column. Each rod is attached to various vertebra along the length of the spine by way of vertebra engaging spinal implants which may include, but are not limited to, pedicle screws, pedicle hooks, transverse process hooks, sublaminar hooks, etc. The spinal implants commonly include a U-shaped rod receiving channel for receiving the longitudinal spinal rod therein. Moreover, the rod receiving channel often includes a means for receiving a fastening mechanism, for example, a set screw or a cam, to subsequent clamp and fix the position of the spinal rod with respect to the spinal implant. With this method, the spinal rod(s) may be shaped to maintain the vertebrae in such an orientation as to correct the spinal disorder at hand (e.g., to straighten a spine having abnormal curvature). Additionally or alternatively, the spinal implants may be spaced along the rods(s) to compress or distract adjacent vertebrae.

Surgeons have, however, often encountered considerable difficulty when using this method, due to problems associated with aligning the spinal rod(s) within the rod receiving channels formed in the heads of the spinal implants. For example, the heads of the spinal implants may be out of vertical and/or horizontal alignment with one another due to the curvature of the spine or the size and shape of each vertebrae.

Thus, there exists a need for a surgical instrument to help facilitate urging the longitudinal spinal rods into the rod receiving channel formed in the spinal implants.

SUMMARY

The present invention may relate to a surgical instrument for urging a longitudinal spinal rod into a top-loading spinal implant, the instrument comprising a holder assembly; a release assembly; and an actuating member operatively associated with the holder assembly and the release assembly so that actuation of the actuating member moves the holder assembly with respect to the release assembly; wherein the release assembly comprises a tubular member and a pusher member, the tubular member is sized and configured to be slidably disposed within the holder assembly, and the pusher member is sized and configured to slidably surround at least a portion of the holder assembly.

The present invention may further relate to a surgical instrument for urging a longitudinal spinal rod into a top-loading spinal implant, the instrument comprising a holder assembly having a pair of fingers including an inward pointing ledge which project radially inwards from an end of the fingers, the ledge being sized and configured to contact an underside of an edge of the spinal implant; a release assembly; and an actuating member wherein the actuating member engages a portion of the holder assembly and a portion of the release assembly so that actuation of the actuating member moves the holder assembly with respect to the release assembly and simultaneously compresses the fingers from a first position to a second position so that fingers contact the underside of the edge of the spinal implant.

The present invention may further relate to a surgical instrument for urging a longitudinal spinal rod into a top-loading spinal implant, the instrument comprising a holder assembly having a proximal end and a distal end; a release assembly having a proximal end and a distal end; and an actuating member having a first tip and a second tip sized and configured to snap onto and engage the proximal end of the holder and release assemblies so that actuation of the actuating member moves the holder assembly with respect to the release assembly.

The holder assembly may also include a pair of fingers for engaging the spinal implant, while the release assembly, for example, the pusher member, may include a recess for engaging the longitudinal spinal rod so that movement of the holder assembly with respect to the release assembly urges the spinal rod into engagement with the spinal implant.

The release assembly may further include a central bore extending from a proximal end to a distal end, the central bore being sized and configured to facilitate insertion of a fastening mechanism into engagement with the spinal implant in order to secure the spinal rod within the rod-receiving channel formed in the spinal implant.

BRIEF DESCRIPTION OF THE DRAWINGS

To facilitate an understanding of and for the purpose of illustrating the present invention, exemplary and preferred features and embodiments are disclosed in the accompanying drawings, it being understood, however, that the invention is not limited to the precise arrangements and instrumentalities shown, and wherein similar reference characters denote similar elements throughout the several views, and wherein:

FIG. 2 is an enlarged side view, partly in section, of the holder assembly of the rod persuader;

FIG. 3 is a top view taken on line 3-3 of FIG. 2;

FIG. 4 is an enlarged side view of the release member of the rod persuader;

FIG. 5 is a top view, partly in section, taken on line 5-5 of FIG. 4;

FIG. 6 is an enlarged side view of the tubular member of the release assembly;

FIG. 7 is a top view, partly in section, taken on line 7-7 of FIG. 6;

FIG. 8 is an enlarged alternate side view of the tubular member of the release assembly;

FIG. 9 is a top view taken on line 9-9 of FIG. 8;

FIG. 10 is a front perspective view of the pusher member of the release assembly;

FIG. 11 is a rear perspective view of the part shown in FIG. 10;

FIG. 12 is a sectional view of the part shown in FIGS. 10 and 11;

FIG. 13 is a front perspective view of an alternate pusher member of the release assembly;

FIG. 14 is a rear perspective view of the part shown in FIG. 13;

FIG. 15 is a sectional view of the part shown in FIGS. 13 and 14;

FIG. 17 is an alternate embodiment of the actuating member;

FIG. 18 is an enlarged perspective view of the actuating member shown in FIG. 17; and FIG. 19 is a partly sectional view showing a vertebra engaging spinal implant that can be used with the rod persuader of FIGS. 1 through 18.

DETAILED DESCRIPTION

For the purposes of promoting an understanding of the principles of the invention, reference will now be made to an exemplary, non-limiting embodiment illustrated in the figures and specific language will be used to describe the same. It will nevertheless be understood that no limitation of the scope of the invention is hereby intended, such alterations and further modifications, and such further applications of the principles of the invention as illustrated herein being contemplated as would normally occur to one skilled in the art to which the invention relates.

Figure 1:
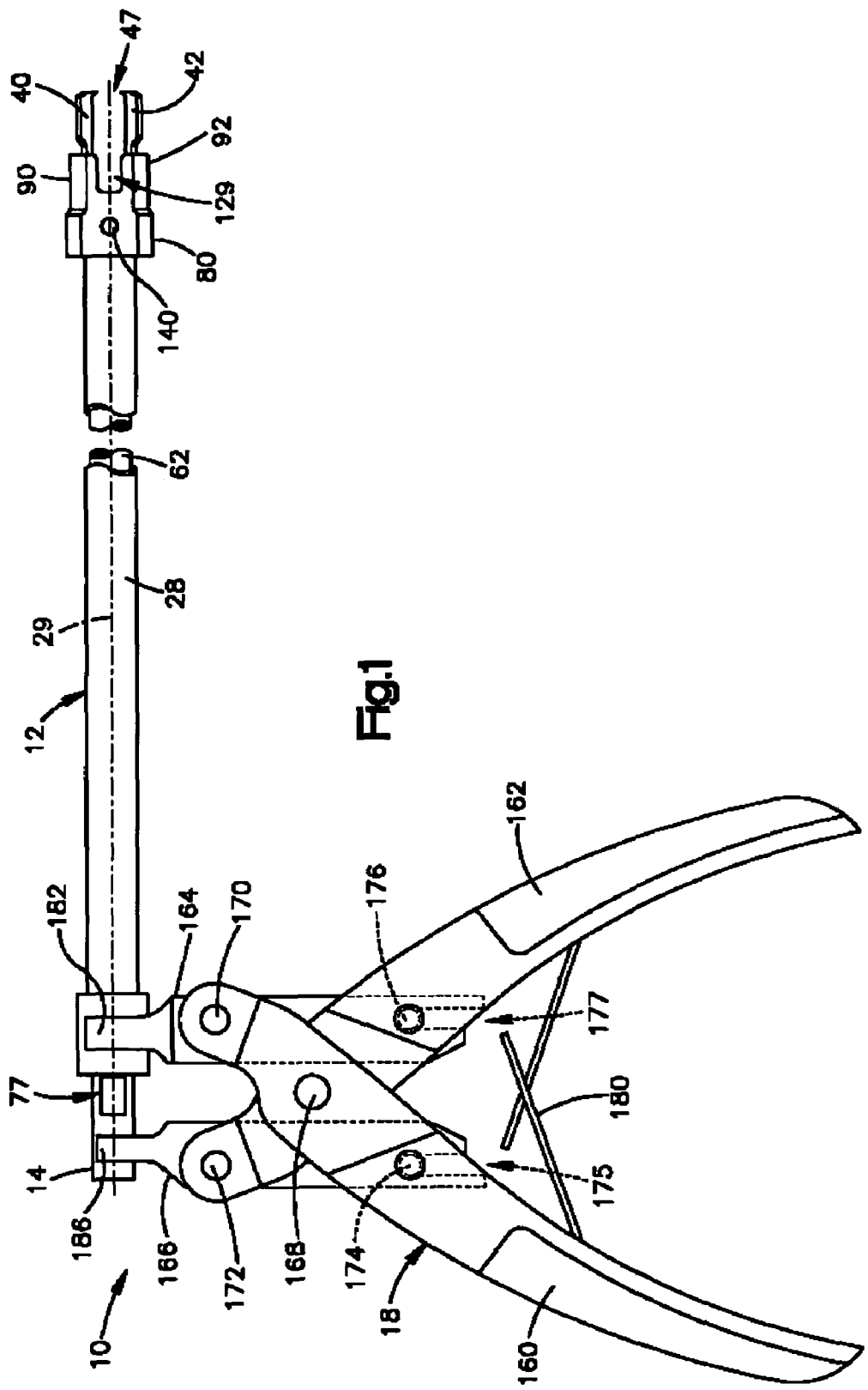
FIG. 1 is a side view of a rod persuader, with actuatable parts of the rod persuader shown in the rest position.

As shown in FIG. 1, the rod persuader 10 is a surgical instrument used by surgeons to urge a spinal rod into a vertebra engaging spinal implant, such as a pedicle screw, a pedicle hook, a transverse process hook, a sublaminar hook, etc. (herein below, referred to generically as a "pedicle screw"). It is contemplated that the rod persuader 10 may be used in conjunction with any pedicle screw so long as the pedicle screw incorporates a top loading U-shaped rod receiving channel sized and configured to receive a longitudinal spinal rod. Preferably, however, the rod persuader 10 is sized and configured to operate in conjunction with polyaxial pedicle screws sold by Synthes Spine® under the trade name AXON®, which is described in pending U.S. patent application Ser. No. 10/682,999 filed on Oct. 14, 2003, entitled *Polyaxial Bone Anchor and Method of Spinal Fixation*, the entire content of which is hereby incorporated by reference.

As shown in FIG. 19, the pedicle screw 200 may comprise, for example, an anchoring member 202, a body 208, and a fastening mechanism 220. The fastening mechanism 220, may be, for example, an externally threaded set screw sized and configured to engage threads formed in the rod-receiving channel 211 so that tightening of the set screw secures the spinal rod 218 within the rod-receiving channel 211.

As shown, the anchoring member 202 and the body 208 may be configured so that the body 208 may be angulated with respect to the anchoring member 202. The anchoring member 202 may include a threaded screw shank 204, a curvate head 206, for example, a spherical head, and a longitudinal central axis 207. The body 208 may include an upper portion 209 incorporating the rod-receiving channel 211 sized and configured to receive the spinal rod 218 therein, and a lower portion 210 defining a recess 212 shaped and dimensioned to receive the head 206 of the anchoring member 202. The recess 212 may include a plurality of slits so that the recess 212 is resiliently compressible in order to permit (1) the body 208 to be snapped over the head 206 of the anchoring member 202 and (2) the body 208 to be fixedly secured with respect to the anchoring member 202 to prevent further movement with respect thereto.

The pedicle screw 200 may further include a locking collar 226 sized and configured to mate with the lower portion 210 of the body 208. The collar 226 may include a tapered inner surface 230 for overlying and mating with a tapered exterior surface 232 formed on the lower portion of the body 208.

Moreover, as shown, the collar 226 may also include an upper edge 228 that extends around the body 208 at a location above the lower end 216 of the rod-receiving channel 211 so that tightening of the fastening mechanism 220 onto the body 208 moves the fastening mechanism 220 against the spinal rod 218 located in the rod-receiving channel 211. Thereby urging the spinal rod 218 against the collar 226 causing the collar 226 to move downward along the exterior surface 232 of the lower portion 210 of the body 208 thereby contracting the recess 212 around the head 206 of the anchor member 202 to secure the angular position of the anchor member 202 with respect to the body 208.

As shown in FIG. 1, the rod persuader 10 may include a holder assembly 12, a release assembly 14, and an actuating member 18. Generally speaking, the actuating member 18 engages and acts upon a proximal end of the holder and release assemblies 12, 14 so that upon actuation, the holder assembly 12 moves with respect to the release assembly 14 so that the longitudinal spinal rod, which is engaged by the release assembly 14, moves toward the pedicle screw, which is located within the holder assembly 12.

The holder assembly 12, which is shown in FIGS. 2 and 3, may include an outer surface 28, a longitudinal axis 29, a proximal end 30, a distal end 32, and a central bore extending therebetween defining an inner surface 26. As shown, the inner surface 26 generally has a uniform diameter along its entire length while the outer surface 28 may include a diametrically enlarged proximal end portion 34. The holder assembly 12 may further include a pair of slots 37 formed in opposite sides of the proximal end portion 34. The slots 37 are sized and configured to receive the actuating member 18 as will be described in more detail later. The proximal end 30 of the holder assembly 12 may also include a pin 38 which extends into the central bore.

The distal end 32 of the holder assembly 12 may include a pair of fingers 40, 42. As shown in FIGS. 2 and 3, the fingers 40, 42 are generally defined by a pair of U-shaped recesses 47, 49 formed in opposite sides of the holder assembly 12. Each of the fingers 40, 42 may also include an inward pointing ledge 56 which projects radially inward from the end of the fingers 40, 42. The ledges 56 are sized and configured to contact the underside of an edge of a pedicle screw. Preferably, the ledges 56 are sized and configured to contact a lower edge 234 of the locking collar 226 of the AXON® pedicle screw in order to pull upwards thereon. As shown, each ledge 56 may include a beveled inner surface 58.

In their normal position, the fingers 40, 42 may be biased apart so that the distance separating the ledges 56 formed at the end of the fingers 40, 42 is greater than the outer diameter of the pedicle screw, for example, greater than the outer diameter of the locking collar 226. This permits the rod persuader 10 to easily slide over and receive the body of the pedicle screw. Alternatively, the fingers 40, 42 may be sized and configured to flex radially outward during insertion of the pedicle screw, and to flex resiliently back inwards toward the pedicle screw after the ledges 56 have cleared the body of the pedicle screw.

Each finger 40, 42 may also include a thickened outer portion 52 and a beveled outer surface 50 which forms a transition from the outer surface of the fingers 40, 42 to the outer surface of the thickened outer portion 52.

As shown in FIGS. 4 and 5, the release assembly 14 may comprise a tubular member 62 and a pusher member 80. One embodiment of the tubular member is shown (without pusher member 80) in FIGS. 6 and 7 and another in FIGS. 8 and 9. The tubular member 62/662 may include an outer surface, a longitudinal central axis 63, a proximal end 64, a distal end 66, and a central bore extending therebetween defining an inner surface 60. The tubular member 62/662 of the release assembly 14 is sized and configured to be slidably disposed within the holder assembly 12.

The proximal end 64 of the tubular member 62/662, may include a first pair of slots 75 sized and configured to receive the actuating member 18, as will be described in more detail later, and a second pair of slots 77, which are sized and configured to overlap with the slots 37 formed on the holder assembly 12 when the tubular member of the release assembly 14 is fully inserted into the holder assembly 12. This facilitates installation of the actuating member 18.

The proximal end 64 of the tubular member 62/662, may also include a slot 72 running generally along the longitudinal axis 63 of the tubular member 62/662 for at least a portion of the member's length. The slot 72 is sized and configured to receive the pin 38 on the holder assembly 12 to serve as a key/guide to help facilitate proper insertion of the tubular member 62/662 into the holder assembly 14. The distal end 66 of the tubular member 62/662 may also include at least one hole 79, and, preferably two holes 79—one on either side of the tubular member 62/662. The hole 79 is sized and configured to receive a pin 140 for securing the pusher member 80 thereto, as will be described in more detail later.

Moreover, as shown in FIGS. 8 and 9, the tubular member 62 may include a diametrically reduced distal portion 67 for engaging the pusher member 80. The diametrically reduced distal portion 67 helps reduce the overall profile of the pusher member 80.

As previously stated, the release assembly 14 includes a pusher member 80. As best shown in FIGS. 10-12, the pusher member 80 is generally a cylindrical member having a proximal end 108, a distal end 110, and a central bore extending therebetween sized and configured to surround at least a portion of the holder assembly 12. The pusher member 80 may further include an upper surface 86, a lower surface 88, and flat planar side surfaces 104, 106 extending from the proximal end 108 to the distal end 110, and from the upper surface 86 to the lower surface 88. As shown, preferably, the side surfaces 104, 106 and the upper and lower surfaces 86, 88 have a smooth transition thereby eliminating all sharp edges.

The proximal end 108 of the pusher member 80 may include at least one circular aperture 111 for receiving a pin 140, and preferably two circular apertures 111 for receiving two pins 140, in order to securely couple the pusher member 80 to the tubular member 62 of the release assembly 14, as best shown in FIG. 5. That is, the at least one pin 140 is sized and configured to extend radially inward through the circular aperture 111 formed in the pusher member 80 and into one of the holes 79 formed in the distal end 66 of the tubular member 62 of the release assembly 14 to secure the pusher member 80 to the tubular member 62. Alternatively, the pusher member 80 may be connected to the tubular member 62 by any means known in the art, including, but not limited to, a set screw, bonding, welding, etc.

The proximal end 108 of the pusher member 80 includes an opening 115 sized and configured to receive the holder assembly 12 coaxially therein. That is, the proximal end 108 of the pusher member 80, preferably, includes an opening 115 formed by curved inner surface portions 116, 118 and oblong outer surface portions 120, 122. The curved inner surface portions 116, 118 are sized and configured to receive the holder assembly 12 along with the tubular member 62 of the release assembly 12, which is slidably disposed within the holder assembly 12. While the oblong outer portions 120, 122 which extend from the curved inner surface portions 116, 118, are sized and configured to receive the fingers 40, 42 formed on the distal end 32 of the holder assembly 12.

The distal end 110 of the pusher member 80 may include a pair of recesses 129 formed therein. As shown, the recesses 129 may be formed in the distal end of the side surfaces 104, 106. The recesses 129 are sized and configured to receive the longitudinal spinal rod therein. The recesses 129 formed within the pusher member 80 are generally configured to extend alongside and overlap the U-shaped recesses 47, 49 formed in the distal end 32 of the holder assembly 12 so that a longitudinal spinal rod may extend completely through the rod persuader 10.

Moreover, the configuration of the recesses 129 creates a pair of diametrically opposed actuator arms 90, 92 that extend axially beside and circumferentially between the recesses 129. The arms 90, 92 are sized and configured to mate with the fingers 40, 42 formed on the holder assembly 12 so that the fingers 40, 42 may project axially through the pusher member 80 at locations that are circumferentially aligned with the actuator arms 90, 92. Preferably, as shown, the arms 90, 92 may also include a beveled inner surface 96, 98 which in combination with the outward bias of the fingers 40, 42 permits the fingers 40, 42 to extend further apart with respect to one another to facilitate engagement with the pedicle screw.

The inner profile of the arms 90, 92 are generally sized and configured to mate with the exterior surface of the fingers 40, 42 formed at the distal end 32 of the holder assembly 12 so that upon movement of the actuating member 18, the fingers 40, 42 compress to contact the underside of an edge of a pedicle screw. That is, upon movement of the actuating member 18, the holder assembly 12 and the release assembly 14 move axially with respect to one another. The sliding interaction between the internal configuration of the arms 90, 92 and the exterior configuration of the fingers 40, 42, compresses the fingers 40, 42 so that the inward pointing ledges 56 formed at the end of each finger 40, 42 compress from a first separation distance to a second separation distance in order for the ledges 56 to contact the underside of an edge of a pedicle screw. More specifically, the interaction between the inner surfaces of the arms 90, 92 formed on the pusher member 80 and the beveled outer surface 50 and thickened outer portion 52 formed on the fingers 40, 42 compress the fingers 40, 42 so that the fingers 40, 42 contact the underside of an edge of a pedicle screw.

An important aspect of the present invention is the concept of gripping the underside of an edge of the pedicle screw rather than gripping the outer side surface of the pedicle screw or a recess formed in the outer side surface of the pedicle screw as disclosed by the prior art. Engaging the underside of an edge of a pedicle screw enables the rod persuader 10 of the present invention to generate a larger reactionary, i.e., upward, force on the pedicle screw than would be possible by gripping the outer side surface or a recess formed in the outer side surface of a pedicle screw. This, in turn, reduces the amount of force required by a user to generate the same force on a patient's anatomy.

Moreover, contacting the underside of an edge of the pedicle screw enables the fingers 40, 42 of the holder assembly 12 to hold the pedicle screw therebetween without fully engaging/clamping the pedicle screw. That is, the fingers 40, 42 are sized and configured to enable the pedicle screw to be loosely held within the fingers 40, 42 at all times. That is, the fingers 40, 42 are sized and configured to permit the pedicle screw to be freely rotatable, transversely moveable and/or axially moveable within the fingers 40, 42.

This provides several advances over prior art devices which either engage the outer side surface of the pedicle screw or engage a recess formed in the outer side surface of the pedicle screw. First, contacting the underside of an edge of the pedicle screw enables the surgeon to adjust the position of the pedicle screw with respect to the spinal rod even after the pedicle screw is located within the rod persuader 10. Second, since the fingers 40, 42 do not fully grip and/or engage the outer side surface or a recess formed in the outer side surface of a pedicle screw, the holder assembly 12 is not prohibited from fully contracting into the pusher member 80 and thus interference with the introduction of the spinal rod into the rod receiving channel of the pedicle screw is eliminated. Third, since the rod persuader 10 does not engage the outer side surface or recesses formed in the outer side surface of the pedicle screw, the fingers 40, 42 are substantially prevented from damaging or chipping the outer surface of the pedicle screw during use thereby helping to maintain the full integrity of the pedicle screw.

Alternatively, as shown in FIGS. 13-15, the pusher member may include two distinct sections 82, 84, namely a proximal section 82 and a distal section 84, extending coaxially along the longitudinal axis 81 of the member 1380. In this embodiment, the inner, and preferably the outer, profile of the arms 1390, 1392 formed in the distal section 84 of the pusher member 1380 are generally sized and configured to be smaller than the inner, and preferably the outer, profile of the proximal section 82 of the pusher member 1380.

Although any actuating member know in the art may be used, preferably, as shown in FIG. 1, the actuating member 18 is a hand grip. The hand grip includes a first grip member 160, a second grip member 162, a first jaw member 164, and a second jaw member 166. The first grip member 160 is pivotally coupled to the second grip member 162 at pivot point 168. The first grip member 160 is also pivotally coupled to the first jaw member 164 at pivot point 170. Similarly, the second grip member 162 is pivotally coupled to the second jaw member 166 at pivot point 172.

Figure 16:
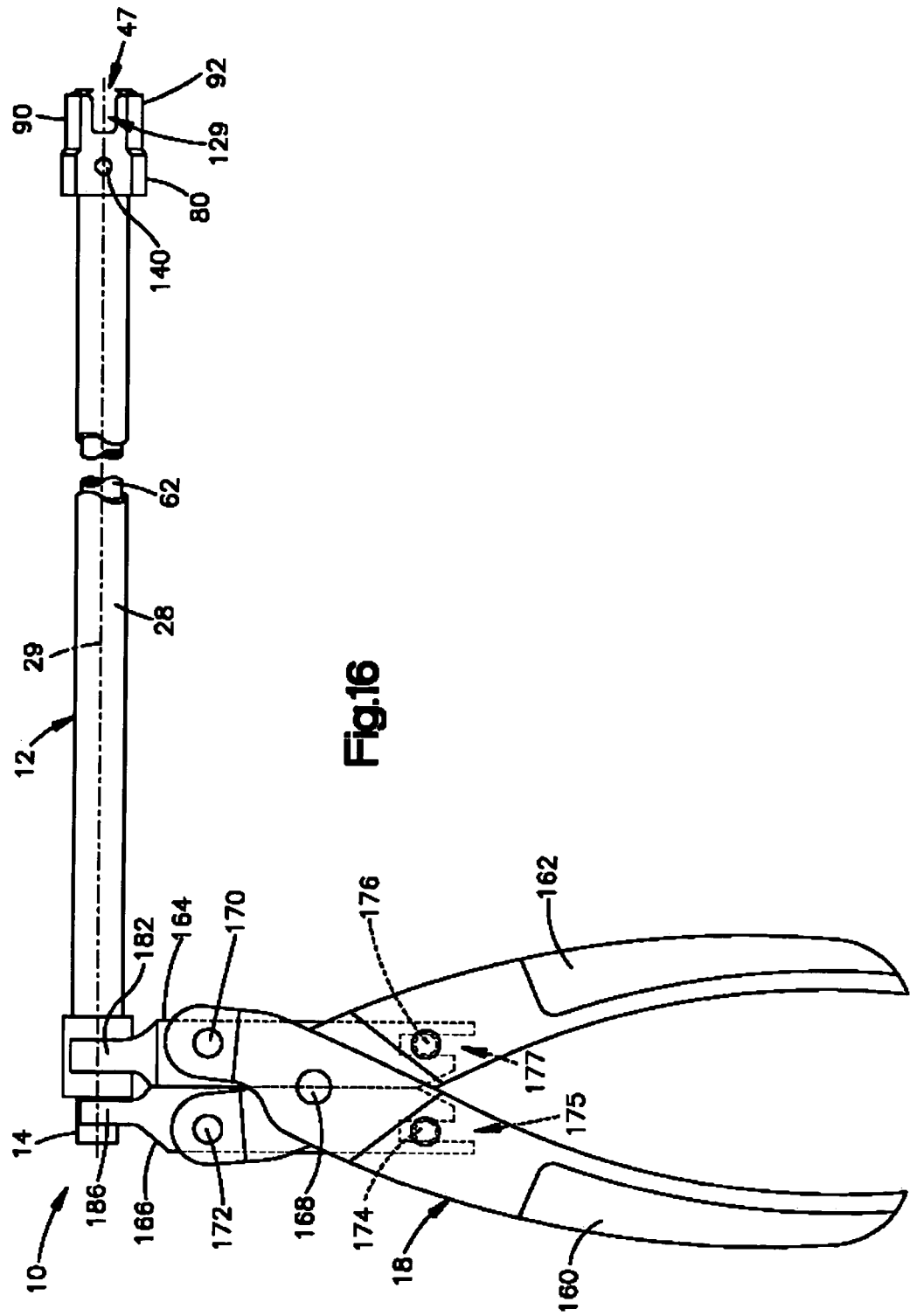
FIG. 16 is a side view of the rod persuader, with the actuatable parts of the rod persuader shown in the actuated positions.

As shown, the first grip member 160 may also include a pin 174 that is slidably movable in a slot 175 formed in the lower end of the second jaw member 166. Similarly, the second grip member 162 may also include a pin 176 slidably movable in a slot 177 formed in the lower end of the first jaw member 164. This pin/slot arrangement maintains the parallel relationship between the first and second jaw members 164, 166 when the hand grip is actuated. In this arrangement, the hand grip may be shifted from the rest position (as shown in FIG. 1) to the actuated position (as shown in FIG. 16) by squeezing the first and second grip member 160, 162 toward each other against the bias of biasing member 180, for example, a spring structure 180 as shown schematically in FIG. 1. The biasing member 180 returns the hand grip to the rest position when the first and second grip members 160, 162 are released.

As shown, the first jaw member 164 includes a tip 182 sized and configured to snap, i.e., clip, onto and engage the slot 37 formed in the holder assembly 12 to fix the holder assembly 12 axially and rotationally relative to the first jaw member 164. Similarly, the second jaw member 166 includes a tip 186 sized and configured to snap, i.e., clip, onto and engage the first slot 75 formed in the release assembly 14 to fix the release assembly 14 axially and rotationally relative to the second jaw member 166. The holder assembly 12 and the release assembly 14 are thus engaged by the hand grip such that at least a portion of the release assembly 14 is slidably disposed within at least a portion of the holder assembly 12 between the rest position (shown in FIG. 1) and the actuated position (shown in FIG. 16) in accordance with corresponding manipulation of the hand grip.

As shown in FIGS. 1 and 16, the hand grip is snapped, i.e., clipped, onto the holder and release assembly 12, 14 so that the hand grip is arranged substantially perpendicular to the longitudinal axes 29, 63 of the holder and release assemblies 12, 14, respectively. Arranging the hand grip perpendicular to the holder and release assemblies 12, 14 provides surgeons with increased visibility of the engagement between the spinal rod and pedicle screw as compared to prior art devices which incorporate actuating assemblies that are in-line and/or in-plane with the surgical instrument. Furthermore, arranging the hand grip perpendicular to the longitudinal axis of the holder and release assemblies 12, 14 permits a surgeon, once the spinal rod has been located with respect to the rod-receiving channel formed in the pedicle screw, to install a fastener mechanism, for example, a set screw or a cam, into engagement with the pedicle screw through the central bore formed in the release assembly 12, as will be described in more detail later.

Moreover, using a hand grip which snaps and/or clips onto the release and holder assemblies 12, 14 enables a surgeon to engage and disengage the hand grip from the assemblies 12, 14 as desired. Thus, for example, a surgeon could disengage the hand grip from the assemblies 12, 14 after completion of the surgical procedure in order to facilitate cleaning of the rod persuader 10.

Alternatively, as shown in FIGS. 17 and 18, the actuating member may be a set of handles. Actuating member 1718 includes handles 250 having a first end 252 and a second end 254, the second end 254 including a bore 256 sized and configured to receive one of the holder assembly 12 or the release assembly 14 therein. Preferably, the bore 256 may be sized and configured to receive the slots 37, 75 formed in the holder and release assembly 12, 14, respectively. The handles 252 are sized and configured to be gripped by a user so that movement of the handles 250 with respect to each other causes the holder assembly 12 to move with respect to the release assembly 14.

In use, the tubular member 62 of the release assembly 14 is slidably received within the holder assembly 12, as shown in FIG. 1, so that movement of the actuating member 18, the holder assembly 12 and the release assembly 14 may move with respect to each other from the rest position shown in FIG. 1 to the actuated position shown in FIG. 16. This, in turn, causes the pusher member 80, and the spinal rod which is engaged thereto, to move downwards with respect to the holder assembly 12 and thus with respect to the pedicle screw which is located between the fingers 40, 42 thereof.

More specifically, after the surgeon has installed the pedicle screws into the vertebra of a patient, a spinal rod is placed longitudinal along the spine in substantial alignment with the pedicle screws. Thereafter, the surgeon, using the rod persuader 10, engages the longitudinal spinal rod within the recesses 129 formed in the pusher member 80. The surgeon further aligns and locates the targeted pedicle screw in-between the fingers 40, 42 of the holder assembly 12. Movement of the actuating member 18 thereafter causes the release assembly 14 to move with respect to the holder assembly 12 causing the fingers 40, 42 to move with respect to the pusher member 80, which forces the fingers 40, 42 to compress so that the ledges 56 formed at the ends of the fingers 40, 42 contact the underside of an edge of the pedicle screw. That is, movement of the release assembly 14 with respect to the holder assembly 12 causes the fingers 40, 42 formed on the holder assembly 12 to be drawn into the pusher member 80 so that the fingers 40, 42 mate with the arms 90, 92 formed on the pusher member 80 of the release assembly 14. Specifically, the beveled outer surface 50 and the thickened outer portion 52 formed on the fingers 40, 42 mate with the inner surface of the pusher member 80 as the fingers 40, 42 move with respect to the arms 90, 92, resulting in the compression of the fingers 40, 42 from a first distance to a second distance, thus causing the ledges 56 formed at the end of each finger 40, 42 to compress and thereby contact the underside of an edge of a pedicle screw.

Simultaneous with the compression of the fingers 40, 42, the holder assembly 12 moves axially upwards and the release assembly 12 moves axially downwards with respect to one another. As the pusher member 80 moves downward toward the pedicle screw, the pusher member 80 engages the longitudinal spinal rod within the recesses 129 formed therein, thereby urging the spinal rod downward into the rod receiving channel formed in the pedicle screw. Thus, the gripping of pedicle screw and the urging of the spinal rod into engagement with the pedicle screw occurs at the same time.

Once the spinal rod is properly located within the rod-receiving channel formed in the pedicle screw, a fastening mechanism, for example, a set screw or a cam, that may permanently fix the spinal rod to the pedicle screw may be installed via the central bore of the tubular member 62. That is, after a surgeon has properly located the spinal rod within the rod receiving channel formed in the pedicle screw, the central bore formed in the release assembly 14 performs the additional function of allowing a surgeon to insert a fastening mechanism through the rod persuader 10 and into engagement with the pedicle screw to permanently affix the longitudinal spinal rod therein.

The present invention has been described in connection with the preferred embodiments. These embodiments, however, are merely for example and the invention is not restricted thereto. Thus, it will be understood by those skilled in the art that other variations and modifications can easily be made within the scope of the invention as defined by the appended claims, thus it is only intended that the present invention be limited by the following claims.

We claim:

1. A surgical instrument for urging a longitudinal spinal member into a top-loading spinal implant, the instrument comprising:
   a holder assembly for engaging the spinal implant, the holder assembly including a proximal end and a distal end, the distal end including a pair of fingers for engaging the spinal implant, the proximal end of the holder assembly including at least one slot;
   a release assembly for contacting the longitudinal spinal member; and
   an actuating member operatively associated with the holder assembly and the release assembly so that actuation of the actuating member moves the holder assembly with respect to the release assembly;
   wherein the release assembly comprises a tubular member and a pusher member, the tubular member being slidably disposed within the holder assembly, and the pusher member slidably surrounding at least a portion of the holder assembly, the tubular member including a proximal end and a distal end, the proximal end of the tubular member including a first pair of slots and a second pair of slots, the pusher member including a recess for engaging the longitudinal spinal member so that movement of the holder assembly with respect to the release assembly urges the spinal member into engagement with the spinal implant; and
   wherein the actuating member includes a first tip and a second tip, the first tip engaging the at least one slot formed on the proximal end of the holder assembly and the second tip engaging the first pair of slots formed on the proximal end of the tubular member and the second pair of slots aligning with the at least one slot formed on the holder assembly when the release assembly is inserted into the holder assembly.

2. The instrument of claim 1 the fingers having a first position in which the spinal implant is freely received therebetween, and a second position in which the fingers contact an underside of an edge of the spinal implant to retain the implant in at least a first axial direction, wherein the fingers are adjustably moveable from the first position to the second position.

3. The instrument of claim 1, wherein the distal end of the holder assembly further includes a pair of U-shaped recesses corresponding with the recess formed in the pusher member so that the spinal member may extend completely through the holder assembly and the pusher member.

4. The instrument of claim 1, wherein the actuating member is moveable between a rest position and an actuated position, the fingers being biased apart in the rest position and contacting an underside of an edge of the spinal implant in the actuated position.

5. The instrument of claim 1, wherein the pusher member has an interior surface and the fingers have an exterior surface to engage the interior surface of the pusher member so that movement of the holder assembly with respect to the release assembly moves the fingers from a first position in which the fingers are separated by a first separation distance to a second position in which the fingers are separated by a second separation distance, the second separation distance being less than the first separation distance.

6. The instrument of claim 5, wherein the fingers engage an underside of an edge of the spinal implant when in the second position.

7. The instrument of claim 1, wherein the distal end of the tubular member includes at least one hole and the pusher member includes at least one aperture, the at least one hole and the at least one aperture receiving at least one pin for securing the pusher member to the tubular member.

8. The instrument of claim 1, wherein the pusher member includes a proximal section and a distal section disposed along a longitudinal axis of the pusher member, the pusher member having an opening to receive the holder assembly coaxially therein.

9. The instrument of claim 1, wherein the tubular member farther includes a central bore extending from a proximal end to a distal end of the member, to receive a fastener.

10. The instrument of claim 1, wherein the tubular member includes a proximal end and a distal end, the proximal end of the tubular member includes a slot to mate with an alignment pin in the proximal end of the holder assembly to facilitate proper alignment of the tubular member within the holder assembly.

11. The instrument of claim 1 further comprising the longitudinal spinal member and the spinal implant, wherein the longitudinal spinal member is a longitudinal spinal rod and the spinal implant comprises:
   a body having a channel for receiving the spinal rod;
   an anchor member associated with the body; and
   a fastener for securing the spinal rod to the body and for fixing the angular position of the anchor member with respect to the body.

12. The instrument of claim 11, wherein the body is a generally cylindrical member having an upper portion incorporating the channel, and a lower portion defining a recess, the anchor member further including a curvate head that is shaped and dimensioned to fit within the recess for facilitating polyaxial movement of the body with respect to the anchor member.

13. The instrument of claim 12, wherein the lower portion of the body surrounding the recess is at least partially compressible to allow the body to be snapped over the curvate head.

14. The instrument of claim 13, wherein the spinal implant further includes a collar slidably disposed around the lower portion of the body, the collar having an inner surface that interacts with an exterior surface of the lower portion of the body to compress the recess around the curvate head when the collar is pressed downward with respect to the body.

15. The instrument of claim 14, wherein the fastener is a set screw having external threads to engage internal threads formed on an inside surface of the upper portion of the body member such that tightening the fastener onto the body moves the fastener against the spinal rod when the rod is located in the channel and urges the spinal rod against the collar causing the collar to move downward along the exterior surface of the lower portion of the body thereby contracting the recess around the curvate head of the anchor member, locking the angular position of the anchor member with respect to the body.

16. The instrument of claim 15, wherein the holder assembly includes a pair of fingers at a distal end thereof, the fingers enabling an axial upward force to be applied to the locking collar.

17. A surgical instrument for urging a longitudinal spinal member into a top-loading spinal implant, the instrument comprising:
   a holder assembly including a proximal end and a distal end, the distal end including a pair of diametrically opposed slots defining a pair of fingers for engaging the spinal implant;
   a release assembly for contacting the longitudinal spinal member, the release assembly including a tubular member and a pusher member, the tubular member slidably disposed within the holder assembly and the pusher member slidably surrounding at least a portion of the holder assembly; wherein the tubular member and the pusher member each comprise a proximal end and a distal end, the distal end of the tubular member includes at least one hole and the pusher member includes at least one aperture, the at least one hole and the at least one aperture receiving at least one pin for securing the pusher member to the tubular member, the pin being displaceable within the pair of diametrically opposed slots formed in the holding assembly; and
   an actuating member operatively associated with the holder assembly and the release assembly so that actuation of the actuating member moves the holder assembly with respect to the release assembly; wherein the actuating member is a hand grip, the hand grip having a first grip member, a second grip member, a first jaw member, and a second jaw member, the first grip member is pivotally coupled to the second grip member, the first grip member is pivotally coupled to the first jaw member, the second grip member is pivotally coupled to the second jaw member, and the first and second jaw members are operatively connected to the holder and release assemblies, respectively;
   wherein the first grip member farther includes a pin slidably movable in a slot formed in the second jaw member and the second grip member includes a pin slidably movable in a slot formed in the first jaw member to maintain the jaw members in parallel alignment when the instrument is actuated; and
   wherein the first and second jaw members further include a tip to snap onto and engage corresponding slots formed in the holder and release assemblies.

18. The instrument of claim 17, wherein when the hand grip snaps onto the holder and release assemblies, the hand grip is orientated substantially perpendicular to the longitudinal axes of the holder and release assemblies.

19. A surgical instrument for urging a longitudinal spinal member into a top-loading spinal implant, the instrument comprising:
   a holder assembly having a proximal end and a distal end;
   a release assembly having a proximal end and a distal end; and
   a hand grip having a first tip and a second tip to snap onto and engage the proximal end of the holder and release assemblies, respectively, so that actuation of the hand grip moves the holder assembly with respect to the release assembly, wherein:
   the hand grip includes a first grip member, a second grip member, a first jaw member, and a second jaw member, the first grip member pivotally coupled to the second grip member, and the first and second jaw members are operatively associated with the holder and release assemblies, respectively;
   wherein the first grip member is pivotally coupled to the first jaw member and the second grip member is pivotally coupled to the second jaw member; and
   wherein the first grip member further includes a pin slidably movable in a slot formed in the second jaw member and the second grip member includes a pin slidably movable in a slot formed in the first jaw member to maintain the jaw members in parallel alignment when the instrument is actuated; and
   wherein when the hand grip snaps onto the holder and release assemblies, the hand grip is orientated substantially perpendicular to the longitudinal axes of the holder and release assemblies.

* * * * *